United States Patent
Kuroda

(10) Patent No.: US 7,505,805 B2
(45) Date of Patent: Mar. 17, 2009

(54) SELF-REFERENCING/BODY MOTION TRACKING NON-INVASIVE INTERNAL TEMPERATURE DISTRIBUTION MEASUREMENT METHOD AND APPARATUS USING MAGNETIC RESONANCE TOMOGRAPHIC IMAGING TECHNIQUE

(75) Inventor: Kagayaki Kuroda, Kobe (JP)

(73) Assignee: Foundation for Biomedical Research and Innovation, Hyogo (JP)

( * ) Notice: Subject to any disclaimer, the term of this patent is extended or adjusted under 35 U.S.C. 154(b) by 222 days.

(21) Appl. No.: 10/564,169

(22) PCT Filed: Jul. 9, 2004

(86) PCT No.: PCT/JP2004/010160

§ 371 (c)(1), (2), (4) Date: Jul. 27, 2006

(87) PCT Pub. No.: WO2005/004718

PCT Pub. Date: Jan. 20, 2005

(65) Prior Publication Data

US 2007/0055140 A1    Mar. 8, 2007

(30) Foreign Application Priority Data

Jul. 11, 2003 (JP) ............................ 2003-273651
Dec. 12, 2003 (JP) ............................ 2003-415330

(51) Int. Cl.
*A61B 5/05* (2006.01)

(52) U.S. Cl. ................... 600/410; 600/407; 324/315; 601/2

(58) Field of Classification Search ............... 600/420, 600/424, 412, 407, 410; 601/2; 324/315, 324/300, 314, 309, 312, 322
See application file for complete search history.

(56) References Cited

U.S. PATENT DOCUMENTS

| | | | |
|---|---|---|---|
| 5,226,418 A | * | 7/1993 | Bernstein et al. ............ 600/419 |
| 5,904,147 A | * | 5/1999 | Conlan et al. .............. 128/899 |
| 6,219,572 B1 | * | 4/2001 | Young ..................... 600/431 |
| 6,445,183 B1 | | 9/2002 | Shimizu et al. |
| 6,566,878 B1 | * | 5/2003 | Komura et al. ............. 324/315 |
| 6,615,069 B1 | | 9/2003 | Komura et al. |
| 2004/0015071 A1 | | 1/2004 | Komura et al. |

* cited by examiner

Primary Examiner—Eric F Winakur
Assistant Examiner—Katherine L Fernandez
(74) Attorney, Agent, or Firm—Armstrong Teasdale, LLP

(57) ABSTRACT

A noninvasive image measuring method of measuring internal organ/tissue temperature using an MRI system. Temperature measurement insusceptible to body motion and spatial variation of magnetic field is realized by utilizing the position and size of a temperature change region as a priori information to determine the phase distribution of the complex magnetic resonance signal of water proton at a given temperature point and by subtracting the phase distribution before the temperature change estimated (self-referred) from the phase distribution in the peripheral region for each pixel of the image, thereby eliminating the subtraction process of image before and after temperature change. The precision of temperature measurement can be enhanced by estimating a complex curved surface formed of the peripheral region in each temperature change region of the real-part and imaginary-part images of the complex magnetic resonance signal, and calculating the phase difference between an actually measured complex signal distribution and the estimated complex signal distribution of the complex signal distribution for each pixel, thereby reducing the estimation error due to phase transition from $-\pi$ to $+\pi$ occurring in a phase distribution. Furthermore, temperature can be measured through optimal imaging following up body motion by using an optical positioning system in combination even if the part being measured is shifted.

36 Claims, 10 Drawing Sheets

Amplitude image

Phase image

Real-part image

Imaginary-part image

Normalized real-part image

Normalized imaginary-part image

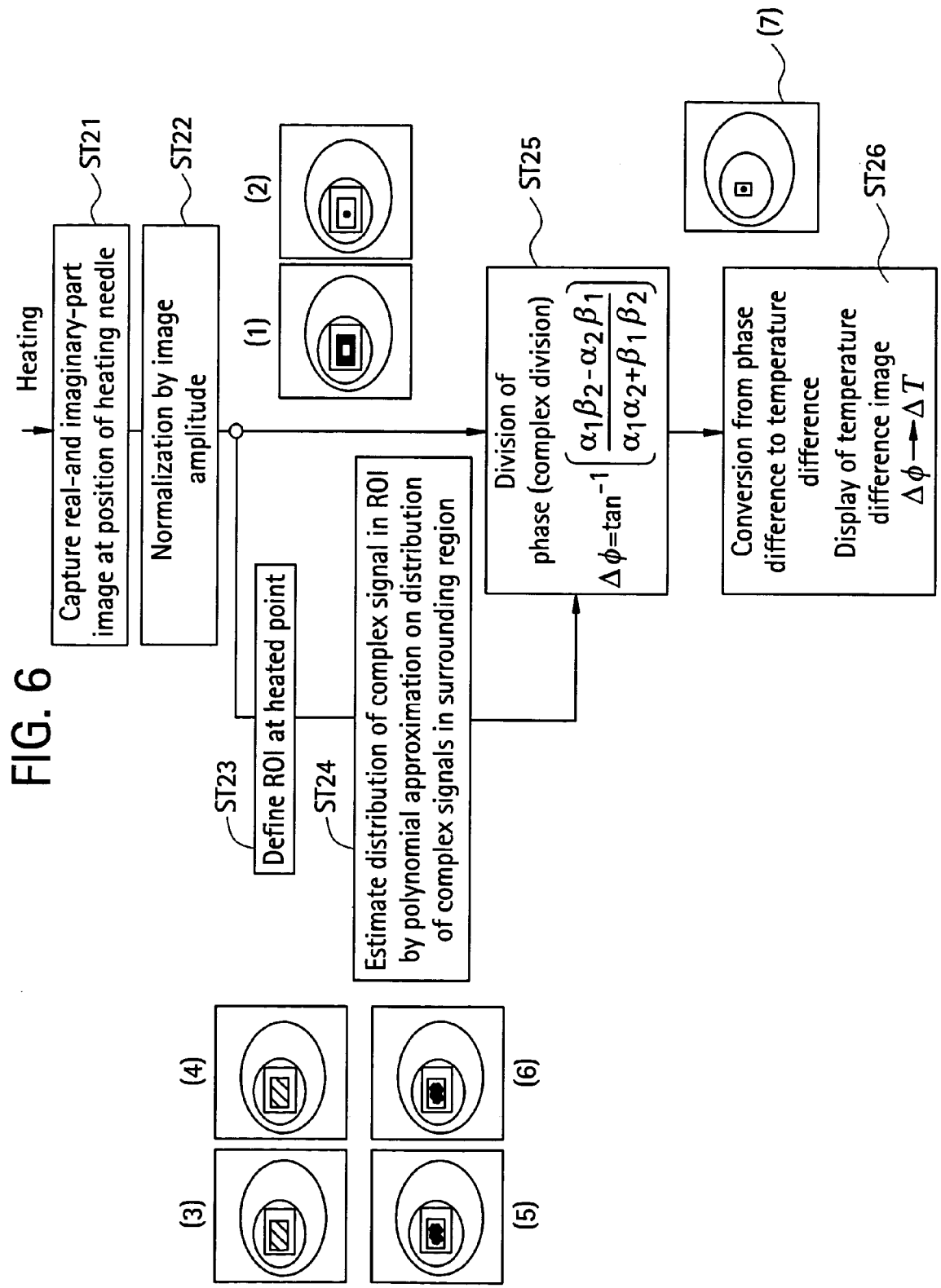

SELF-REFERENCING/BODY MOTION TRACKING NON-INVASIVE INTERNAL TEMPERATURE DISTRIBUTION MEASUREMENT METHOD AND APPARATUS USING MAGNETIC RESONANCE TOMOGRAPHIC IMAGING TECHNIQUE

CROSS REFERENCE TO RELATED APPLICATIONS

This application claims the benefit of PCT/JP2004/010160 filed Jul. 9, 2004.

BACKGROUND OF THE INVENTION

The present invention relates to a non-invasive measurement method for an internal organ/tissue temperature using a magnetic resonance imaging (MRI) technique, and a method of capturing an optimal MRI image using an optical positioning apparatus during thermotherapy or cryotherapy.

SUMMARY OF THE INVENTION

Therapeutic methods against cancers include thermotherapy such as thermoablation, hyperthermia, and the like, in which heating apparatuses employing microwaves, radio frequency (RF) waves, laser or focused ultrasound have been used in need of convenient heating on a localized tumor. Since in such thermotherapy the tumor region to be treated must be heated above a certain temperature while a normal region must be kept below a certain temperature, it is important to accurately measure the temperature of the tumor and normal regions in the living body for heating control.

Monitoring of the temperature in thermotherapy has been generally achieved by a probe such as a thermocouple or fiber-optic probe penetrating into a tumor. Such an invasive method of temperature measurement, however, have many severe problems including that: it impairs low invasiveness otherwise inherent in thermotherapy; it cannot detect an abnormally high temperature point that may appear outside a measured point; penetration of a probe involves a risk of metastasis of tumor cells; and a probe may interact with electromagnetic waves or ultrasound used for heating.

To solve these problems, a technique for non-invasive imaging of an internal temperature distribution has been desired. An MRI temperature measurement method has several advantages including that: a three-dimensional region can be arbitrarily selected; MRI has a variety of temperature-dependent parameters; MRI is safe in that it involves no irradiation; and MRI does not require external injection of a contrast material. Furthermore, MRI surpasses other tomographic imaging techniques in its ability of discrimination on soft tissue containing a tumor, and it is also advantageous in observation of a change in tissue (degeneration of protein, edema formation, necrosis, etc.) during an operation or in evaluation of the effect of therapy.

Known MRI temperature-dependent parameters include thermal equilibrium magnetization ($M_0$), a longitudinal relaxation time ($T_1$), a transverse relaxation time ($T_2$), a constant of diffusion (D), and a chemical shift ($\delta$). Comparing these parameters for imaging a temperature distribution, first, as temperature dependence of the proton density varies with the type or condition of tissue, macroscopic magnetization varies due to magnetic components, and accordingly, a thermal property of $M_0$ incorporating an effect of the proton density varies with the type or condition of tissue. Similarly, temperature dependence of $T_1$ significantly varies with the type or condition of tissue so that the sign of the temperature factor sometimes becomes inverted. This is because $T_1$ is a function of viscosity and a variety of proteins contained in water in living tissue governs the property of $T_1$ in a complicated manner through bonded water, free water or proton exchange between them. $T_2$ has almost not been studied as a temperature parameter because it generally has a poorer S/N in measurement than that of $T_1$. D is thought to be more suitable for temperature measurement than $T_1$ because D is governed by translational diffusion that is sensitive to temperature, as opposed to $T_1$ being affected principally by rotational diffusion of molecules, and D is determined from a ratio between two magnetic resonance echo signals and thus is insusceptible to spatial inhomogeneity of excitation magnetic field pulses. However, D is measured using a long echo time, which leads to a poor S/N, and is susceptible to temporal instability of static magnetic field intensity and body motion.

A proton chemical shift is similar to $T_1$, $T_2$ and D in that its temperature dependence results from Brownian motion, but different from them in that its variation comes through electromagnetic factors, such as hydrogen bonds and a hindrance effect of electron clouds. Although water protons are not only protons that have temperature-dependent $\delta$, it is advantageous to use water protons in clinical applications because of their strongest signal intensity. The term chemical shift as used herein refers to a ratio of a difference between an appropriate reference frequency and a magnetic resonance frequency of protons in a specific component or group, to the reference frequency. Previous studies have reported that the chemical shift $\delta$ of water protons in cell suspension, tissue extracted from a mouse, brain of swine, etc. is proportional to the temperature with a negative factor ranging from $-0.007$ to $-0.01$ ppm/° C., as compared to the temperature factor of a of pure water being $-0.01$ ppm/° C., and therefore, a difference in temperature dependence of the chemical shift $\delta$ of protons among tissue is smaller than that in the other parameters. As used herein, ppm is abbreviation of parts per million ($\times 10^{-6}$). That is, by $-0.01$ ppm/° C. is meant that a temperature change of 1° C. causes the phase to change in a rate of $-1 \times 10^{-8}$.

Furthermore, since all of the other parameters are measured based on an amplitude, they interfere with one another in a finite measurement time and separate measurement is difficult; on the other hand, the proton chemical shift $\delta$ is alone a parameter that is based on a frequency and can be measured separately from the other amplitude-based parameters. Thus, the proton chemical shift $\delta$ is a parameter that is currently believed to be most suitable for temperature measurement.

There have been known two techniques of imaging a temperature distribution using the water proton chemical shift: a spectroscopic imaging technique and a phase imaging technique. In brief, the spectroscopic imaging technique is suitable for measurement of a temperature change that is slow and over a wide range because it is possible to avoid an effect of variation in tissue magnetization or of body motion by employing an internal reference, although it requires a long measurement time. On the other hand, the phase imaging technique cannot avoid an effect of magnetization or body motion, but quick and convenient temperature measurement is possible. The phase imaging technique directed to a local and steep temperature change induced by laser or focused ultrasound has received attention and is being intensely studied.

A resonance frequency is a frequency of rotational motion of a macroscopic magnetization vector, and can be translated into an amount of rotation of the phase of the macroscopic magnetization vector in a certain period of time. Since magnetic resonance signals are detected as complex signals, the amount of rotation of the phase of the magnetization vector can be measured as a phase of signals in a complex plane (an arctangent $\tan^{-1}$ of the ratio between a real part and an imaginary part). As the temperature increases (decreases) the phase angle decreases (increases) according to a change in resonance frequency. Thus, an imaging technology sometimes referred to as gradient magnetic field echo technique is employed to determine a chemical shift difference $\Delta\delta_W$ using a difference $\Delta\phi_W$ between a phase at a reference temperature and that after a temperature change in each voxel, and a temperature difference is measured using the following equation:

$$\Delta T = \frac{\Delta\delta_w}{\alpha} = \frac{\Delta\phi_w}{\omega_{RF} \cdot TE \cdot \alpha}$$

where TE (sec) is a period of time from a center of an excitation magnetic field pulse to an echo signal center (echo time), $\alpha$ (ppm/° C.) is a temperature factor of a chemical shift, and $\omega_{RF}$ is a reference frequency (rad/sec) of a receiver system in an apparatus. Since the gradient magnetic echo feature is standard equipment in clinical MRI systems, the phase imaging technique has an advantage that it can be conveniently practiced using existing hardware.

A method of imaging a temperature distribution of internal organ or tissue by observing complex signals from water protons using MRI and detecting phase variation due to a temperature change is disclosed in Patent Document 1 (Japanese Patent Application KOHYO No. 2003-511122), which is a magnetic resonance imaging method comprising separately identifying the position of a measurement point, and modifying a magnetic resonance image based on the identified position, whereby translational motion of an object to be examined causes almost no disturbance.

Non-patent Document 1 ("Front Line of Neurosurgery, Advanced Medical Series 2: Neurosurgery" by Kagayaki KURODA, published by Advanced Medical Technology Laboratory, pages 226-233 (May, 2000)) discloses non-invasive image measurement of an in-brain temperature distribution using MRI. Non-patent Document 2 (K. Kuroda, K. Oshio et al., A chemical shift selective phase mapping method, Magn. Reson. Med., pp. 845-851 (1997)) discloses a temperature measurement method comprising imaging the phase of proton magnetic resonance signals of a reference material at a certain temperature point in the first time, and imaging the phase of water proton magnetic resonance signals in the second time to obtain the phase difference therebetween; and Non-patent Document 3 (K. Kuroda, K. Oshio et al.: Temperature Mapping Using Water Proton Thermal Shift: Self-Referenced Method with Echo Planar Spectroscopic Imaging, Magn. Reson. Med., 43, pp. 220-225 (2000)) and Non-patent Document 4 (K. Kuroda, N. Takei et al., Feasibility of Internally-Referenced Temperature Imaging Using Metabolite Signals, Magn. Reson. Med. Sci., 2, 1, pp. 17-22 (2003)) disclose a method of measuring a temperature change as variation in the frequency difference by determining a frequency difference between a reference material and water at each temperature point on a pixel-by-pixel basis.

Furthermore, Patent Document 2 (Japanese Patent No. 3346800) discloses means of estimating a water proton chemical shift by estimating at least one of a frequency or a spectrum of magnetic resonance signals acquired in MRI.

On the other hand, a therapeutic case in the prior art in which an optical positioning apparatus is employed to guide a microwave heating needle to a tumor in a liver for thermotherapy is disclosed in Non-patent Document 5 (S. Morikawa, T. Inubushi et al., MR-guided microwave thermocoagulation therapy of liver tumors: initial clinical experiences using a 0.5 T open MR system, J. Magn. Reson. Imaging, 16, pp. 576-583 (2002)). In this technique, a microwave heating needle is attached with an optical positioning apparatus, and is guided to a tumor in a liver identified by MRI while checking the position of the tip of the heating needle, allowing a clinician to control the direction and length of penetration of the heating needle while viewing a monitor. Since the heating needle can be reliably guided to a tumor inside an organ once the heating needle has been inserted, unnecessary damage to the organ by, for example, the heating needle inserted into an organ many times or too deep is prevented, thus improving clinical utility of thermotherapy.

DISCLOSURE OF THE INVENTION

In the conventional temperature measurement methods by a phase imaging technique using MRI, the temperature is measured based on subtraction of the phase of a reference image before a temperature change from an image after a temperature change, and therefore, the temperature cannot be measured if the body of the subject moves between the times before and after a temperature change, or if an object to be imaged is abdominal organ such as liver that moves with respiration, or if an organ moves or deforms for a reason other than respiratory motion, because reliability of an estimated temperature value is significantly corrupted. Thus, in such cases, a temperature change of organ subjected to thermoablation etc. cannot be imaged during treatment, and quantitative temperature control is difficult. Moreover, to identify the position of a measurement point, a micro coil as in Patent Document 1 must be disadvantageously inserted into the medical patient.

As described in Non-patent Document 1, if a brain, which is contained in a hard cranium and undergoes no mechanical motion, is to be measured, its position is almost completely fixed by fixing the head and accurate arithmetic processing can be achieved; however, a large blood flow rate, and a change in blood flow rate and blood oxidization rate due to activation may lead to a change in tissue magnetic susceptibility. The change in tissue magnetic susceptibility due to activation is as much as ca. 0.05 ppm, which corresponds to a temperature change of about 5° C. The sensitivity to such a change in tissue magnetic susceptibility is another drawback of the phase imaging technique.

A method of estimating a water proton chemical shift using a temperature-independent parameter of Patent Document 2 is directed to overcoming of such drawbacks, although the method requires sequential measurement of magnetic resonance signals, their frequency or spectrum following a time series. Moreover, the methods disclosed in Non-patent Documents 3-5 require signal integration for measuring referential signals because they employ a low concentration of a reference material. Thus, these techniques are impractical as a temperature measurement method conducted on the human body or non-human animal body for a heated region during thermotherapy because, for example, it takes a long time to conduct one imaging session in these methods, and motion during an imaging session at one temperature point (intra-scan motion) prevails over an effect of motion between imaging sessions at different temperatures (inter-scan motion).

An optical positioning apparatus has been conventionally used only for the purpose of introducing a heating needle or the like to a tumor, as described in Non-patent Document 5.

While in thermotherapy, for example, a plurality of anatomical images can be captured by an MRI apparatus to check the position of the tumor and heating needle or the like based on the image, it is also possible to accurately guide the heating needle or the like to the tumor by attaching the optical positioning apparatus to the heating needle or the like.

Therefore, an object to be achieved by the present invention is to provide a method and an apparatus for measuring a temperature change of internal organ or tissue by which the aforementioned problems in the conventional temperature measurement method according to the phase imaging technique using MRI are solved, and which is unaffected by body motion by incorporating an optical positioning apparatus.

To attain the aforementioned objects, the present invention images a temperature distribution of an object to be measured only by complex magnetic resonance signals from water protons at a certain temperature, without using a reference image. Specifically, the present invention comprises: imaging a phase distribution after a temperature change; inputting by an operator a priori information therefrom with respect to the position of a portion at which a temperature change takes place to a computer; defining by the computer the portion at which a temperature change takes place as a region of interest based on the information; estimating a curved surface formed by the phase distribution of complex magnetic resonance signals from water protons in the region of interest before a temperature change; and subtracting the estimated phase distribution image from the measured phase distribution image on a pixel-by-pixel basis. Since temperature information contained in a phase distribution image is obtained by self reference using a priori information (the position and size of the region at which a temperature takes place) from the image itself, a process of subtraction of the phase distribution between two images at different temperatures is eliminated, thus avoiding an effect of motion of the region to be measured between the times before and after a temperature change. It should be noted that the term self reference as used in the present invention refers to recursive reference based on a priori information.

In another aspect of the present invention, it is possible to reduce an estimation error due to phase transition from $-\pi$ to $+\pi$ occurring in a phase distribution, by estimating a complex curved surface formed of a complex signal distribution in a region of interest in a real-part image and an imaginary-part image of complex magnetic resonance signals, and calculating a phase difference between a measured complex signal distribution and an estimated complex signal distribution on a pixel-by-pixel basis.

In still another aspect of the present invention, an optical positioning apparatus, which has been conventionally used by a clinician to control the direction or degree of penetration of a heating needle or the like into a medical patient, is employed in combination with the aforementioned temperature measurement method for the purpose of knowing the position of organ or tissue after guiding the heating needle or the like to a target position, whereby a temperature of organ or tissue can be measured while constantly tracking a heated point in thermoablation, for example. Thus, a temperature change in organ or tissue subjected to body motion such as respiratory motion can be measured and imaged without inserting a temperature measuring or position identifying instrument into the body, which was impossible in the conventional techniques.

The non-invasive imaging method for measuring a temperature of internal organ or tissue according to the present invention is capable of measuring a temperature of internal organ or tissue by using the method without capturing a separate reference image or using a phase distribution in the reference image as a reference phase, and moreover, is capable of measuring a temperature of internal organ or tissue without being affected by body motion. Thus, in thermotherapy on organ or tissue that moves with body motion, for example, accurate temperature measurement on a heated portion can be achieved, thus providing a clinical effect that a temperature change during the treatment can be visualized for heating control. Moreover, since cross sections in one or more orthogonal planes or parallel planes including a heated portion can be imaged even if organ or tissue moves, an accurate volumetric temperature distribution around the heated portion during thermotherapy can be known during the treatment, thus providing another clinical effect that a therapeutic effect of thermotherapy can be enhanced by optimal heating control. The same clinical effects can also be attained in cryotherapy.

BRIEF DESCRIPTION OF DRAWINGS

FIG. 6 is a flow chart of a temperature measurement program in accordance with Embodiments 2 and 3 of the present invention.

FIG. 8(A) shows a microwave heating needle penetrating into a swine liver sample while feeding direct current (15 mA) to a small-diameter coil wound over the needle; FIG. 8(B) shows determination of a plane perpendicular to the needle by detecting a dark point caused by magnetic field inhomogeneity due to the direct current; and FIG. 8(C) shows a resulting temperature distribution obtained in the perpendicular plane using the inventive method.

BEST MODE FOR CARRYING OUT THE PRESENT INVENTION

Several embodiments of the present invention will now be described with reference to the accompanying drawings.

Embodiment 1

Figure 1:
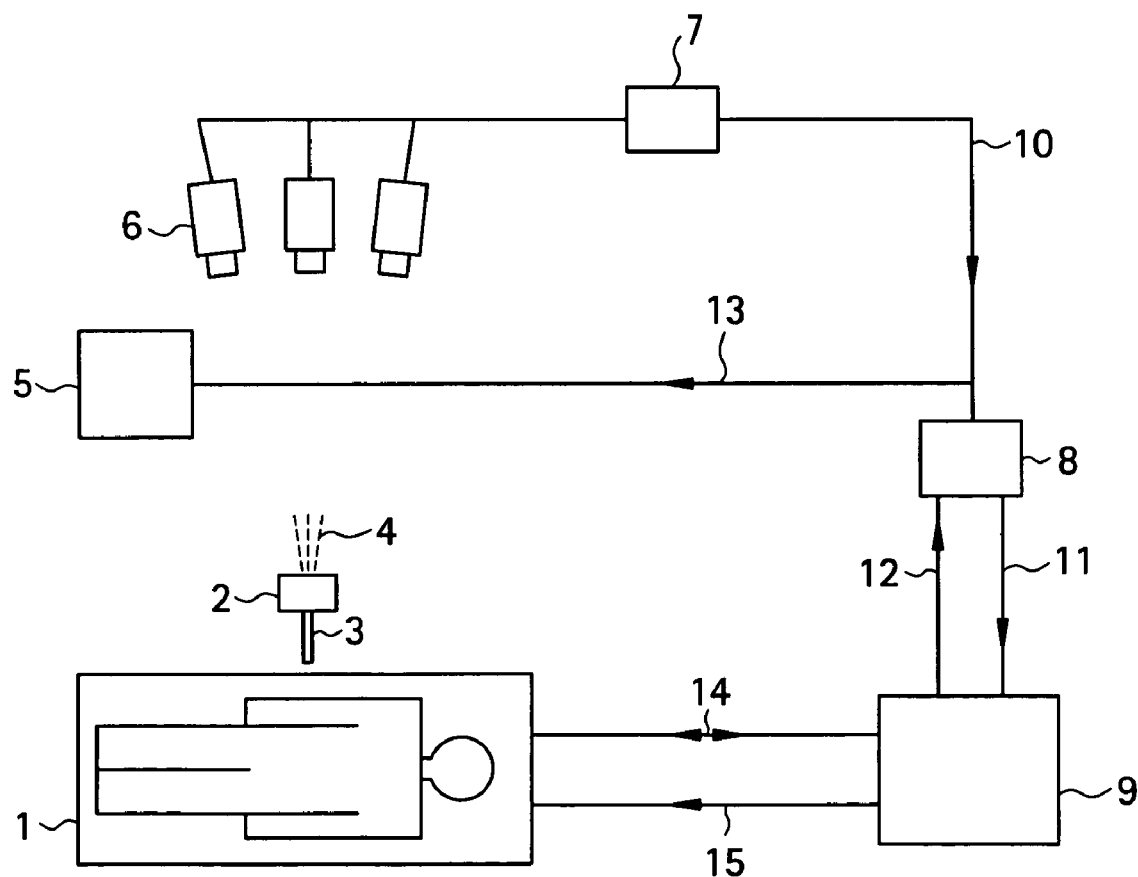
FIG. 1 is a configuration diagram of an MRI apparatus etc. used in the present invention.

To begin with, a configuration of a medical MRI apparatus etc. used in the present invention is shown in FIG. 1. The MRI apparatus is attached with an optical positioning apparatus, and infrared radiation 4 emitted by the optical positioning apparatus 2 is imaged by a video camera 6 mounted over the MRI apparatus main portion. The infrared radiation captured by the video camera 6 is converted into a position control signal 10 by a sequential logic box 7 for calculating a position of a probe 3 in a heating needle or the like attached to the optical positioning apparatus 2, and sent to a workstation 8. A personal computer can be employed as the workstation 8. The position control signal 10 is transmitted to an MR imaging control unit 9 via the workstation 8 as an imaging plane adjusting electric signal 11 for controlling an imaging plane. The MRI apparatus main portion 1 and MR imaging control unit 9 communicate RF signals 14 and gradient pulses 15 for capturing a phase distribution image. If no optical positioning apparatus is employed because the object to be measured is fixed, an imaging plane is controlled by the workstation 8 to image the position of the probe checked by an MRI image. RF signals sent from the MRI apparatus main portion 1 are converted into image data 12 by the MR imaging control unit 9 and sent back to the workstation 8, then to a monitor 5 as image data 13, allowing a clinician to conduct heating control in thermotherapy or the like while viewing the image on the monitor.

Figure 2:
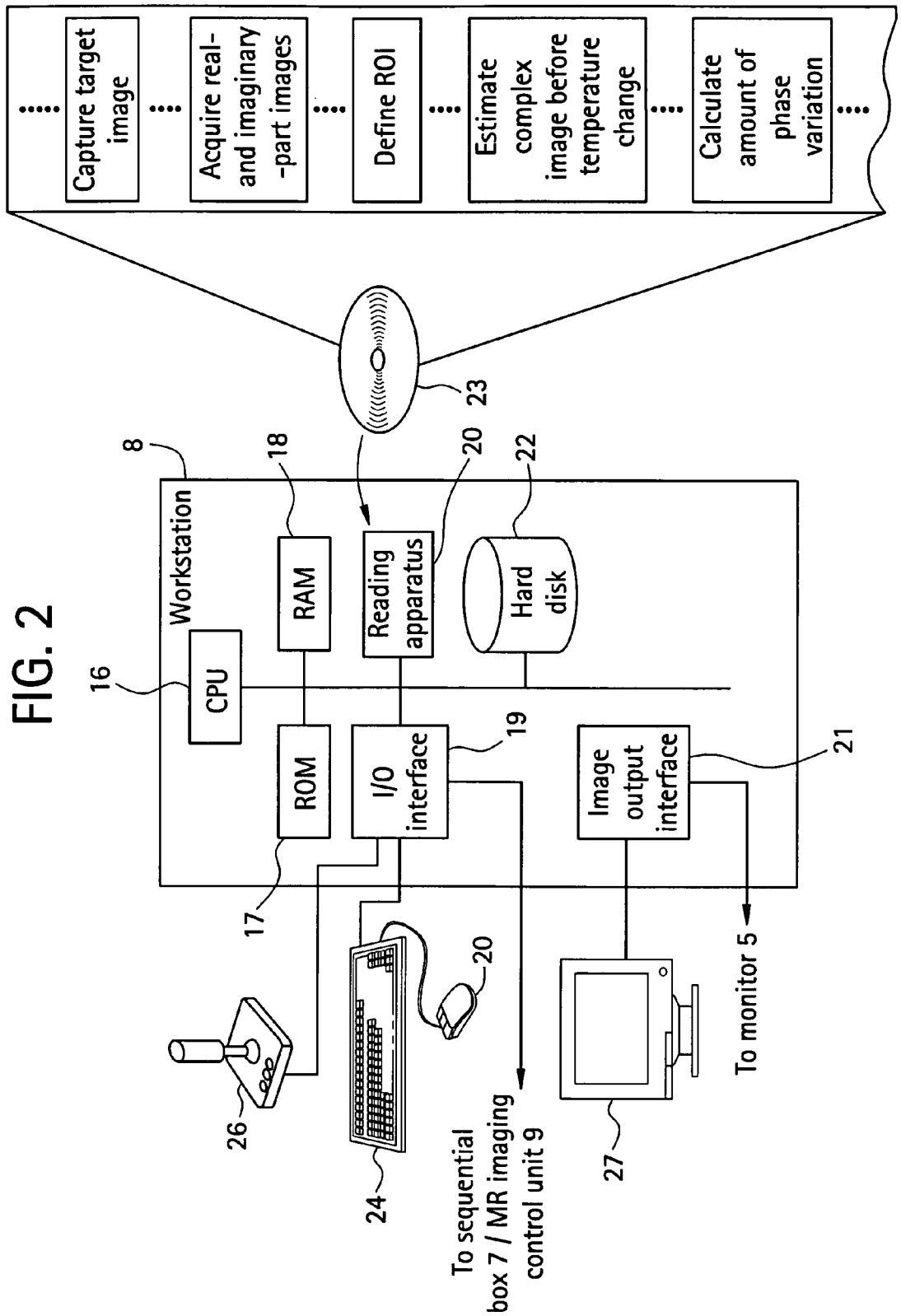
FIG. 2 is a block diagram showing a configuration of a workstation in the MRI apparatus used in the present invention.

FIG. 2 is a block diagram showing a configuration of the workstation 8 shown in FIG. 1. The workstation 8 is mainly comprised of a CPU 16, a ROM 17, a RAM 18, an input/output interface 19, a reading apparatus 20, an image output interface 21, and a hard disk 22.

The CPU 16 is capable of executing a program stored in the ROM 17 and/or a program loaded in the RAM 18. By the CPU 16 executing a computer program for practicing the method of the present invention, which will be discussed later, the MRI apparatus and the like shown in FIG. 1 serve as the temperature measurement apparatus in accordance with the present invention.

The ROM 17 is comprised of a mask ROM, a PROM, an EPROM, an EEPROM or the like, in which programs executed by the CPU 16, data used therein and the like are recorded.

The RAM 18 is comprised of an SRAM, a DRAM or the like. The RAM 18 is used for reading programs recorded in the ROM 17 and hard disk 22. Moreover, it is used as a working area for the CPU 16 executing these programs.

The hard disk 22 is installed with several kinds of programs such as an operating system and application programs to be executed by the CPU 16 and data used in execution of the computer programs. The hard disk 22 is also installed with a computer program for practicing the method of the present invention.

The reading apparatus 20 is comprised of an FD (flexible disk) drive, a CD-ROM drive, a DVD-ROM drive or the like, for reading the computer programs recorded in a portable recording medium 23 such as an FD for practicing the present invention. It is also possible to record the computer programs for practicing the method of the present invention in the portable recording medium 23, cause the workstation 8 to read the computer program for practicing the method of the present invention from the portable recording medium 23, and install the computer program into the hard disk 22.

The input/output interface 19 is comprised of a serial interface such as for example USB, IEEE 1394 and RS-232C, a parallel interface such as SCSI, IDE and IEEE 1284, or an analog interface comprising a D/A or A/D converter. The input/output interface 19 is connected with a keyboard 24 and mouse 25 attached to the workstation 8, and also with a controller 26 as needed; by operating these input devices, information regarding adjustment of an imaging plane and definition of a region of interest, etc. can be supplied to the workstation 8. Moreover, the input/output interface 19 is connected with the sequential logic box 7 and MR imaging control unit 9 to receive the position control signal 10 from the sequential logic box 7, and transmit/receive the imaging plane adjusting signal 11 and image data 12 to/from the MR imaging control unit 9.

The image output interface 21 is connected to an image display device 27 comprising an LCD or CRT, for outputting image data supplied from the CPU 16 to the image display device 27. The image display device 27 displays an image according to the supplied image data. Moreover, the image output interface 21 is also connected to the monitor 5 attached to the MRI apparatus main portion 1, allowing the clinician etc. to view an MR image during treatment.

Next, an operation of the temperature measurement apparatus in accordance with an embodiment of the present invention will be described. The workstation 8 loads a computer program for practicing the method of the present invention, which will be described below, from the hard disk 22 to the RAM 18, and causes the CPU 16 to execute the program, whereby the MRI apparatus and the like shown in FIG. 1 including the workstation 8 serve as the temperature measurement apparatus in accordance with the present invention.

Flow charts depicting computer program procedures for practicing the conventional and inventive methods of measuring a temperature of internal organ or tissue using the MRI apparatus are shown in FIG. 3.

Figure 3B:
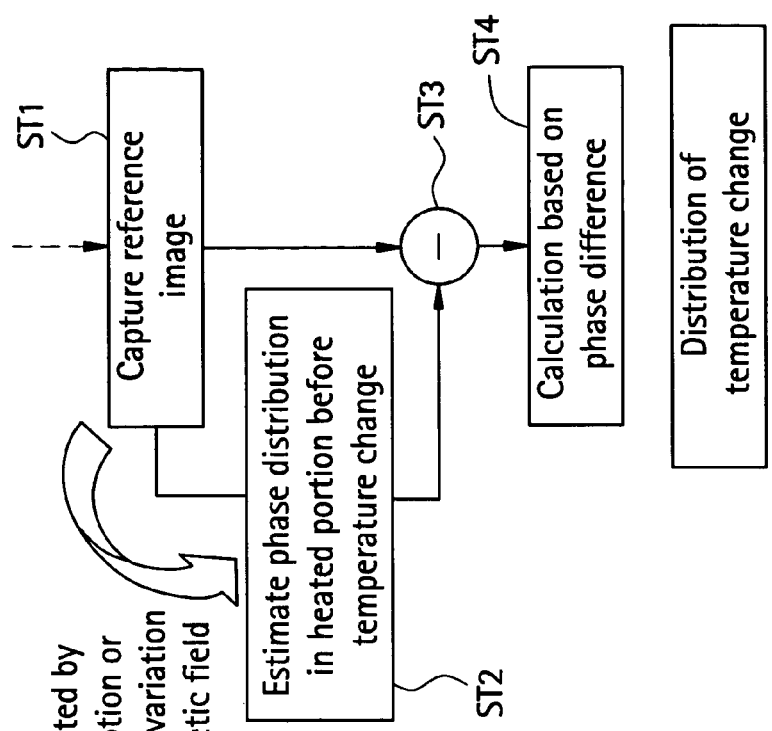
FIG. 3 is a flow chart of a temperature measurement program in accordance with a conventional technique and Embodiment 1 of the present invention.
Figure 3A:
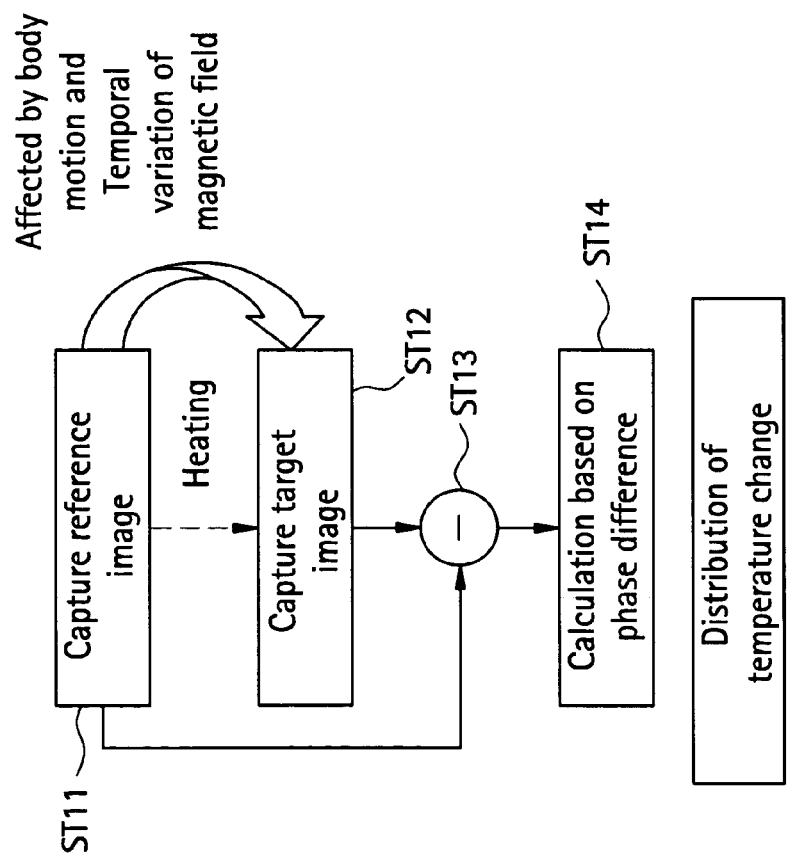

According to the conventional method (FIG. 3(A)), a phase distribution is imaged before a temperature change, i.e., before thermotherapy on organ or tissue, and the distribution image is defined as a reference phase distribution image (Step ST11). Thermotherapy or the like is then conducted, a phase distribution is again imaged after a temperature change in a tumor inside the organ or tissue, and the distribution image is defined as a target phase distribution image (Step ST12). A phase difference between the images is then calculated by subtracting the reference phase distribution image from the target phase distribution image on a pixel-by-pixel basis (Step ST13), and based on the phase difference, a temperature distribution is measured (Step ST14). It should be noted that the subtraction at Step ST13 is achieved by the same calculation method as that at Step ST3 of the present invention.

Since in the conventional method, the phase distribution is imaged before and after thermotherapy, there should be a temporal difference between the reference phase distribution image and target phase distribution image, and in the interim, organ or tissue may move or the magnetic field tends to vary, leading to a drawback of inaccurate temperature measurement. Moreover, to accurately perform the pixel-by-pixel subtraction, the imaging plane must be fixed and organ or tissue to be measured must remain at the same position and in the same shape.

As opposed to that, according to the present invention (FIG. 3(B)), thermotherapy or the like is first conducted on organ or tissue, and a phase distribution image of the organ or tissue is captured at a certain temperature point after a temperature change. During thermotherapy or the like, an in-body penetrating portion of a heating or cooling apparatus is accurately guided to a tumor region based on an MRI image. The tumor region is then imaged to capture a temperature change, and a baseline phase image is obtained at the temperature point (Step ST1). The baseline phase image is a phase image including a portion at which a temperature change takes place, and since the position at which a temperature takes place is known beforehand as the vicinity of the tip of the initially checked in-body penetrating portion of the heating apparatus or the like, the operator inputs advance information on the position of the vicinity of the in-body penetrating portion to the computer to cause the computer to define the vicinity of the tip as a region of interest based on the information, and estimate a phase distribution in the region of interest from a phase distribution in a portion surrounding the region of interest (Step ST2). This estimation is applicable to organ or tissue that has a nearly homogeneous interior with a sufficiently larger portion that undergoes no temperature change than a portion at which a temperature change takes place, such as, for example, a liver. Specifically, since in such organ or tissue, phase variation is smooth around the region of interest in which a temperature change takes place, and thermotherapy or the like will not result in a temperature change all over the organ or tissue, a phase distribution in the region of interest can be mathematically estimated from a phase distribution in a portion surrounding the region of interest by applying higher-order rational polynomial fitting by a linear least squares method, functional fitting by a non-linear least squares method, a finite element method or the like.

Next, complex conjugates of the phase in the baseline phase image and estimated phase image are multiplied with each other and an arctangent ($\tan^{-1}$) of the product is calculated to thereby subtract the estimated phase image from the baseline phase image on a pixel-by-pixel basis and measure a phase difference in the region of interest (Step ST3).

Finally, a distribution of a temperature change is determined from the phase difference distribution (Step ST4). Similarly in cryotherapy, a temperature distribution in the region of interest can be obtained, although a temperature drops in the region of interest. The temperature change in the region of interest thus obtained can be output to a monitor or the like superimposed over an anatomical image of organ or tissue captured by MRI.

The temperature change measurement apparatus of the present invention comprises: means of acquiring a measured phase distribution image of organ or tissue at a certain temperature point after a temperature change corresponding to Step ST1; means of defining a region of interest including a certain position in the acquired measured phase distribution image, means of estimating a phase distribution of complex magnetic resonance signals before a temperature change in the region of interest based on a phase distribution of complex magnetic resonance signals in a portion surrounding the region of interest, and means of producing an estimated phase distribution image based on the estimated phase distribution corresponding to Step ST2; means of calculating the amount of phase variation by conducting subtraction between the measured phase distribution image and estimated phase distribution image on a pixel-by-pixel basis, and means of producing a phase distribution image representing the amount of phase variation of complex magnetic resonance signals caused by the temperature change in the region of interest corresponding to Step ST3; and means of calculating a temperature change from the phase distribution image representing the amount of phase variation corresponding to Step ST4; these means are all implemented by calculating input signals at the workstation 8 shown in FIG. 1, and the calculation is conducted by reading the means into the calculating apparatus.

The method of estimating a phase distribution at Step ST2 of the present invention will now be particularly described. The estimation of a phase distribution according to the present invention refers to a process of assuming a mathematical model representing a phase distribution, and optimizing the model based on measured data. For example, if a cubic function is employed as a mathematical model representing a phase distribution in rational function fitting by a linear least squares method (for simplification, only a one-dimensional spatial direction is considered here), the process comprises optimizing coefficients in a model function as follows:

$$\hat{\phi} = ax^3 + bx^2 + cx + d$$

based on measured data, and the coefficients a-d are determined such that a residual square sum of a value of the model function and the measured value is minimized. In practice, a phase distribution is estimated by considering such a rational function in two-dimensional spatial directions and conducting fitting to a curved surface, rather than a curved line. In this case, although the coefficients may be fitted to functions having the same order in X- and Y-directions, they may be fitted to functions having different orders.

Figure 4:
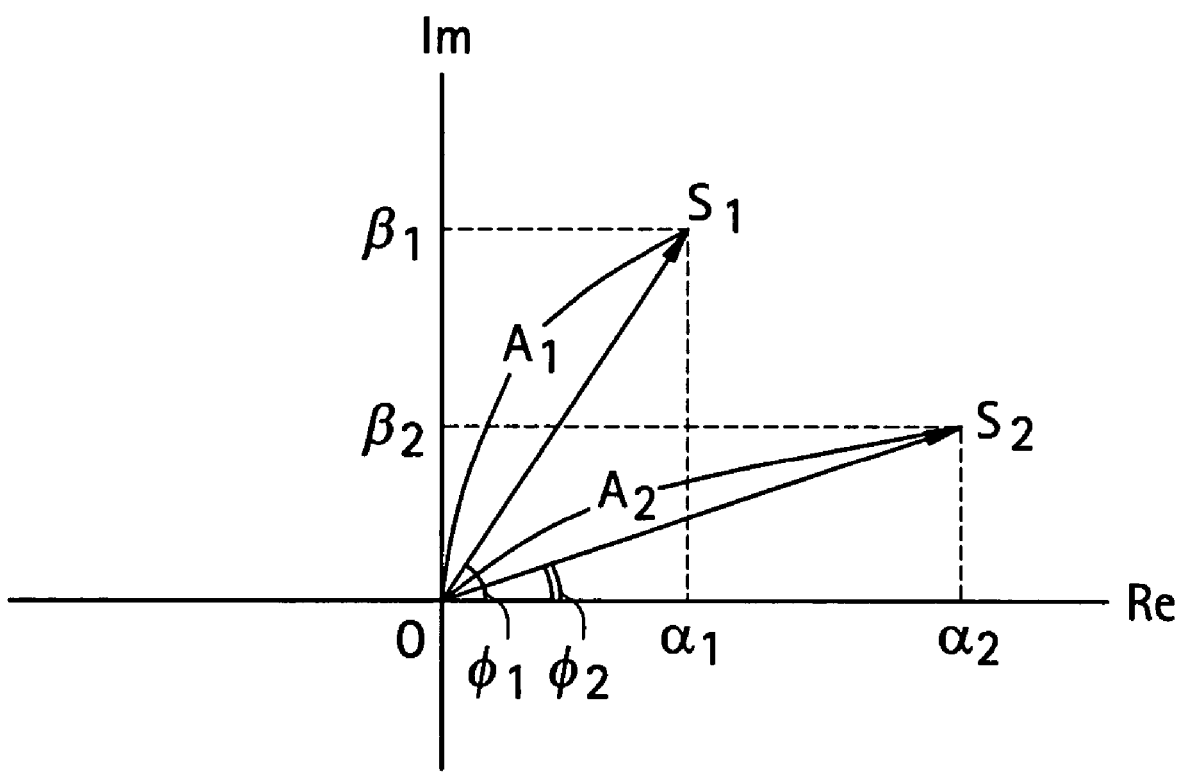
FIG. 4 is a conceptual diagram of phase variation due to a temperature change.

Next, FIG. 4 will be referred to to particularly explain subtraction of a phase distribution at Step ST3 of the present invention and at Step ST13 of the conventional method. In FIG. 4, a horizontal axis represents a real part (Re), and a vertical axis represents an imaginary part (Im). In FIG. 4, $\phi$ designates a phase, S designates a complex magnetic resonance signal and A designates an amplitude, and a subscript 1 represents a value before a temperature change and a subscript 2 represents a value after a temperature change.

Before a temperature change, a relationship: $S_1 = \alpha_1 + j\beta_1$ holds. Since $\alpha_1 = A_1 \cos \phi_1$ and $\beta_1 = A_1 \sin \phi_1$, $S_1 = A_1 \exp(j\phi_1)$ is obtained from the Euler's formula $\exp(j\phi) = \cos \phi + j \sin \phi$; Similarly, after a temperature change, $S_2 = A_2 \exp(j\phi_2)$ is obtained. While the phase difference can be determined from $\phi_2 - \phi_1 = \tan^{-1}(S_2) - \tan^{-1}(S_1)$, if, for example, $\phi_1$ is $-0.6\pi$ and $\phi_2$ is $0.8\pi$, simple subtraction gives $\phi_2 - \phi_1 = 0.8\pi - (-0.6\pi) = 1.4\pi$. However, taking account of the fact that the original phase is calculated by an arctangent function ($\tan^{-1}$) having a return value $[-\pi, \pi]$, the subtraction is $\phi_2 - \phi_1 = 0.8\pi - (-0.6\pi + 2\pi) = -0.6\pi$ by rights. Thus, to conduct phase subtraction including a case of two phase values across the border between the second and third quadrants of a complex plane (a negative portion of a real axis), according to the present invention, phase subtraction employing complex conjugates as given below is introduced, as in the conventional method. Specifically, multiplying $S_2$ with a complex conjugate of $S_1$ gives:

$$S_1^* \cdot S_2 = A_1 \exp(-j\phi_1) \cdot A_2 \exp(j\phi_2)$$
$$= (\alpha_1 - j\beta_1)(\alpha_2 + j\beta_2)$$
$$= \alpha_1\alpha_2 + \beta_1\beta_2 + j(\alpha_1\beta_2 - \alpha_2\beta_1),$$

and then, $$\phi_2 - \phi_1 = \arg(S_1^* \cdot S_2)$$
$$= \tan^{-1}\{(\alpha_1\beta_2 - \alpha_2\beta_1)/(\alpha_1\alpha_2 + \beta_1\beta_2)\}$$

can be obtained. In this equation, arg designates a phase angle, and * represents a complex conjugate. Since in the equation, the phase difference is obtained as a function value of $\tan^{-1}$, a correct phase difference can be calculated without correction of $2\pi$. The phase difference is a dimensionless amount, and its unit is radian (rad). Substituting EQ. 1 with the phase difference $\phi_2-\phi_1=(\Delta\phi_W)$ obtained by the calculation method, a temperature difference $\Delta T$ can be obtained.

According to the temperature measurement method of the present invention, since a temperature of a heated point is measured by self-referencing one phase distribution image at a certain temperature point, it is possible to completely exclude an effect of body motion and magnetic field variation that could not be avoided in the conventional method even by fixing the object to be measured. Moreover, since only a phase distribution chart of a water proton chemical shift is imaged, the imaging time is as short as ca. two seconds, and it is possible to significantly reduce the imaging time as compared to a method of estimating a phase distribution from the proton's resonance frequency of a material other than water that requires about one minute for one image. Thus, accuracy of temperature measurement is drastically improved.

Embodiment 2

The configuration of a temperature measurement apparatus in accordance with the present embodiment is similar to that of Embodiment 1.

An amplitude image, a phase image, a real-part image and an imaginary-part image obtained from a complex image captured in one plane including a human liver are shown in FIGS. 5(A)-5(D), respectively.

In Embodiment 1, a phase image before a temperature change is estimated from a reference phase image after a temperature change, and a phase distribution may contain a portion in which phase transition from $-\pi$ to $\pi$ occurs. Thus, if phase transition occurs in the vicinity of a portion at which a temperature change takes place, i.e., in a portion surrounding the region of interest, a phase distribution in a portion surrounding the region of interest becomes rough. Then, an estimation error increases in estimating a phase distribution in the region of interest from a phase distribution in a portion surrounding the region of interest at Step ST2. For example, while in the amplitude image of FIG. 5(A) usually used in diagnosis, the liver can be observed on the left side of the image, there occurs phase transition in the liver, especially in the X-direction, in the phase image of FIG. 5(B).

Since a phase difference is $$\Delta\phi_W = \phi_2 - \phi_1 = \arg(S_1^* \cdot S_2)$$
$$= \tan^{-1}(S_1^* \cdot S_2),$$

the phase difference $\Delta\phi_W$ can also be directly calculated using complex magnetic resonance signals $S_1$ and $S_2$. In other words, if complex magnetic resonance signals $S_1$ before a temperature change can be directly estimated from complex magnetic resonance signals $S_2$ after a temperature change, a phase difference can be calculated without estimating the phase.

Since $S_2=\alpha_2+j\beta_2$, $\alpha_2=A_2\cos\phi_2$ and $\beta_2=A_2\sin\phi_2$, there is given $S_2=A_2\cos\phi_2+jA_2\sin\phi_2$, and a spatial distribution of $S_2$ is continuously represented by a function having a cos-type real part and a sin-type imaginary part. Thus, rather than estimating a phase distribution before a temperature change by directly applying higher-order rational polynomial fitting by a linear least squares method and the like to a phase distribution after a temperature change, a region of interest is defined in the same position in a real-part image and an imaginary-part image of complex magnetic resonance signals $S_2$ after a temperature change, a distribution of real-part resonance signals and imaginary-part resonance signals in the region of interest is estimated from a distribution of measured real-part resonance signals and measured imaginary-part resonance signals in a portion surrounding the region of interest to estimate complex magnetic resonance signals $S_1$ before a temperature change, whereby an effect of phase transition from $-\pi$ to $+\pi$ occurring in the phase distribution can be eliminated, and a temperature change in the region of interest can be more accurately measured from a phase difference between phases before and after a temperature change.

According to the present embodiment, the same position in a real-part image and an imaginary-part image is defined as a region of interest so as to include a portion at which a temperature change takes place, and a real-part image and an imaginary-part image before a temperature change are estimated based on a distribution of real-part and imaginary-part signals in a portion surrounding the region of interest.

Embodiment 3

The configuration of the temperature measurement apparatus in accordance with the present embodiment is similar to that in Embodiments 1 and 2.

Since in a measured real-part image and a measured imaginary-part image, fat tissue etc. having a high water content is bright and bones etc. having a low water content is dark, smoothness of the signal distribution may sometimes be corrupted by brightness. Now normalizing a measured real-part image and a measured imaginary-part image by dividing them by an amplitude $A_2$ on a pixel-by-pixel basis in the aforementioned Embodiment 2, $S_2/A_2=\cos\phi_2+j\sin\phi_2$ is obtained, in which the right-hand side is expressed only by cos and sin functions. In other words, a real-part image and an imaginary-part image independent of a distribution of brightness are obtained. By using thus-normalized real-part and imaginary-part images, still more accurate estimation of real-part resonance signals and imaginary-part resonance signals in the region of interest can be obtained, and a temperature change in the region of interest can be more accurately measured from a phase difference after a temperature change. Particularly, normalization is performed by dividing the real-part image of FIG. 5(C) and the imaginary-part image of FIG. 5(D) by the amplitude image of FIG. 5(A) on a pixel-by-pixel basis.

Figure 5A:
FIG. 5 shows an amplitude image (A), a phase image (B), a real-part image (C), an imaginary-part image (D), a normalized real-part image (E), and (E) a normalized imaginary-part image obtained from a complex image captured in a certain plane containing a liver of a human subject.
Figure 5B:
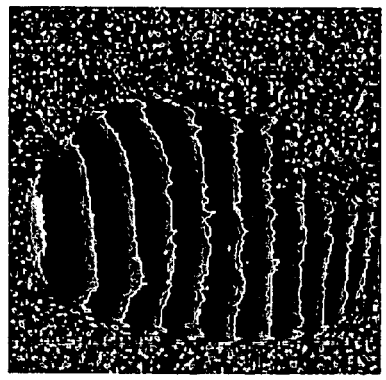
Figure 5C:
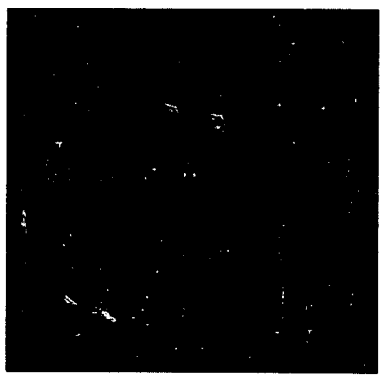
Figure 5D:
Figure 5E:
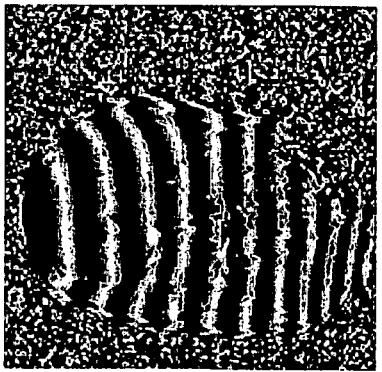
Figure 5F:
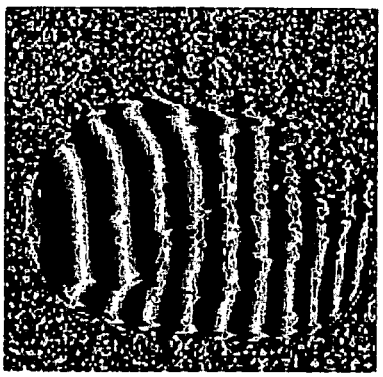

Normalized versions of the images of FIGS. 5(C) and (D) are show in FIGS. 5(E) and 5(F), respectively. The normalized real-part/imaginary-part images have a value of one in the brightest portion and minus one in the darkest portion (as an amplitude of cos and sin functions). In FIGS. 5(E) and (F), these values are assigned to highest and lowest brightness in the image to determine grayscales. Comparing FIGS. 5(E) and (F) with the phase image shown in FIG. 5(B), edges of streaks become smooth and fitting with a rational function is facilitated.

A flow chart depicting a program procedure for practicing the method of measuring a temperature of internal organ or tissue in Embodiments 2 and 3 of the present invention is shown in FIG. 6.

Thermotherapy or the like is conducted on organ or tissue, a real-part image and an imaginary-part image of complex magnetic resonance signals from the organ or tissue are captured at a certain temperature point after a temperature change, and a measured real-part image and a measured imaginary-part image of a tumor region are obtained at the temperature (Step ST21). If more accurate temperature measurement is to be conducted, the measured real-part image and measured imaginary-part image are subsequently divided by an amplitude on a pixel-by-pixel basis for normalization to eliminate an effect of brightness (Step ST22). Since the measured real-part image and measured imaginary-part image are images including a portion in which a temperature change takes place, an operator inputs advance information on the position of the vicinity of the tip of the heating apparatus or the like to the computer, and the computer defines the vicinity of the tip as a region of interest based on the information (Step ST23). A signal distribution in the region of interest in the measured real-part image and measured imaginary-part image after a temperature change is estimated from a signal distribution in a portion surrounding the region of interest in a similar manner to that at Step ST2 (Step ST24). Since in the estimation at Step ST24, real-part resonance signals are distributed in a cos-type continuous function and imaginary-part resonance signals are distributed in a sin-type continuous function as described above, the estimation has higher accuracy than that at Step ST2 of Embodiment 1 in which a phase distribution is estimated, because the estimation at Step ST24 is insusceptible to phase transition.

Next, complex magnetic resonance signals $S_1$ before a temperature change are estimated from the estimated real-part image and estimated imaginary-part image, and a phase difference between $S_1$ and $S_2$ is calculated on a pixel-by-pixel basis (Step ST25). In particular, at Step ST25, $$\phi_2 - \phi_1 = \arg(S_1^* \cdot S_2)$$
$$= \tan^{-1}\{(\alpha_1\beta_2 - \alpha_2\beta_1)/(\alpha_1\alpha_2 + \beta_1\beta_2)\}$$

is calculated on a pixel-by-pixel basis as in Step ST3 of Embodiment 1. Specifically, complex conjugates of complex magnetic resonance signals are multiplied with each other, and an arctangent of a ratio between a real part and an imaginary part of the product is calculated to calculate a phase difference between the measured complex image and estimated complex image on a pixel-by-pixel basis.

Finally, a distribution of a temperature change is determined from the distribution of the phase difference (Step ST26).

The temperature change measurement apparatus in accordance with Embodiment 2 of the present invention comprises: means of acquiring a measured real-part image and a measured imaginary-part image of measured complex magnetic resonance signals of organ or tissue at a certain temperature point after a temperature change corresponding to Step ST21; means of defining a region of interest including a certain position in the acquired measured real-part image and measured imaginary-part image corresponding to Step ST23; means of estimating a real-part distribution and an imaginary-part distribution of complex magnetic resonance signals in the region of interest before a temperature change based on the real-part distribution and imaginary-part distribution of complex magnetic resonance signals in a portion surrounding the region of interest corresponding to Step ST24; means of calculating the amount of phase variation by calculating a phase difference between the measured complex image and estimated complex image on a pixel-by-pixel basis, and means of producing a phase distribution image representing the amount of phase variation of complex magnetic resonance signals caused by a temperature change in the region of interest corresponding to Step ST25; and means of calculating a temperature change from the phase distribution image representing the amount of phase variation corresponding to Step ST26; these means are all implemented by calculating input signals at the workstation 8 shown in FIG. 1, and calculation is conducted by reading the means into the calculating apparatus.

The temperature change measurement apparatus in accordance with Embodiment 3 of the present invention further comprises means of normalizing the measured real-part image and measured imaginary-part image by dividing them by an amplitude on a pixel-by-pixel basis corresponding to Step ST22, in addition to the means described above.

Embodiment 4

Next, description will be made hereinbelow on a method of capturing a desired optimal MRI complex image by identifying a position of heated point or cooled point in thermotherapy or cryotherapy following body motion using an optical positioning apparatus, which is another object of the present invention. The key to success of thermotherapy: or cryotherapy is heating or cooling control based on accurate temperature measurement of a heated or cooled portion; in the conventional temperature measurement method according to a phase imaging technique, a temperature is measured based on subtraction of a reference phase image before a temperature change from a target phase image after a temperature change as described above, and therefore, if the object to be measured moves between the times before and after a temperature change, reliability of the estimated temperature value is significantly corrupted to inhibit temperature measurement.

Figure 7:
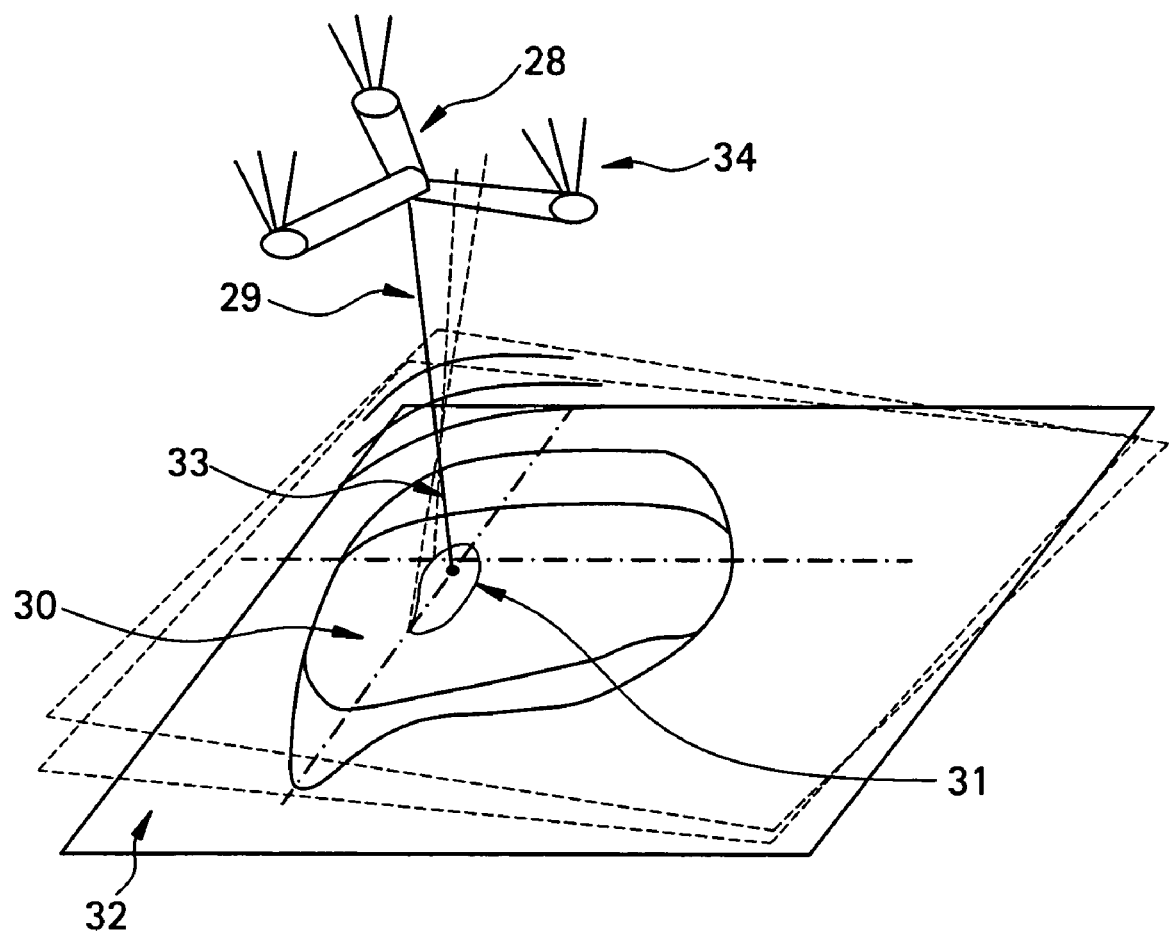
FIG. 7 is a schematic diagram showing a method of attaching an optical positioning apparatus in the method of the present invention.

FIG. 7 is a schematic diagram of a method of attaching an optical positioning apparatus during thermotherapy on a liver tumor in an animal subject, including a human subject, in accordance with the method of the present invention. According to the present invention, an optical positioning apparatus 28 is perpendicularly attached to an upper portion of a heating needle 29 of a heating apparatus in thermotherapy. The tip of the heating needle is guided to a tumor 31 in a liver 30, which is a point to be heated, using an MRI image. Thereafter, as the tip of the heating needle, i.e., the tumor (heated point) 31, moves with body motion, the top surface of the optical positioning apparatus also moves, with the tip of the heating needle acting as an effort point, an abdominal wall acting as a fulcrum, and the optical positioning apparatus acting as a resistance point. By detecting infrared radiation 34 emitted from three LED's on the top surface of the optical positioning apparatus by a video camera attached to the MRI apparatus, the orientation of the top surface of the optical positioning apparatus can be known, and since the tumor lies at a position perpendicularly away from the center of the positioning apparatus by a length of the heating needle, the position of the tumor can be accurately known regardless of body motion. Thus, it is possible to change an imaging cross-sectional plane 32 according to motion of the tumor. The same applies to cryotherapy.

Particularly, an MRI apparatus has MRI coordinate axes: an X-axis in a right-and-left (horizontal) direction of a subject, a Y-axis in a front-and-back (vertical) direction, and a Z-axis in an up-and-down (opposite) direction. On the other hand, the optical positioning apparatus also has its coordinate axes: a Y-axis in a direction perpendicular to the apparatus, a Z-axis in a direction along a stick portion to which a referential LED is attached, and an X-axis in a direction perpendicular to these axes. Since the MRI coordinate axes are fixed, infrared radiation emitted from the LED of the optical positioning apparatus can be detected by a video camera attached to an upper portion of the MRI apparatus to thereby detect motion of the optical system coordinate axes, and the computer incorporated in the MRI apparatus can match the MRI coordinate axes with the optical system coordinate axes. By such matching by the computer when the heating needle or the like moves with movement of the organ or the like, imaging in an orthogonal imaging plane intersecting an extension of the heating needle or the like including the tip of heating needle or the like at which a temperature change takes place can be achieved following body motion. Moreover, by capturing a plurality of complex images in planes parallel to the orthogonal plane, it is possible to three-dimensionally know a temperature distribution.

On the other hand, since the heating needle or the like is perpendicularly attached to the center of the optical positioning apparatus, imaging in parallel planes at a certain angle with respect to the optical positioning apparatus can be achieved even if organ or the like moves. Moreover, by capturing a plurality of complex images at a plurality of angles, it is possible to know a temperature distribution in a direction horizontal with respect to the heating needle or the like.

In continuous imaging in mutually orthogonal planes, the planes are determined to include a heated point at their respective centers. Specifically, the planes are determined such that the heated point lies at an intersection of the two or three orthogonal planes. While the angle of the group of planes is arbitrarily selected except that they should be selected such that any one of them does not include the heating needle, it is most preferably 45° so that an angle formed between a plane and the heating needle or the like is large for every plane. Specifically, taking an axis of the heating needle or the like as a reference, an imaging plane is determined such that all normal vectors of the three mutually orthogonal planes form 45° with respect to a direction vector of the axis. While imaging in parallel planes may be done at an arbitrary angle except that any one of the planes should not include the heating needle, it is most preferably 90°.

Furthermore, since the optical positioning apparatus can be used to conduct imaging such that the tip of the heating needle or the like, i.e., a position at which a temperature change takes place, tracks body motion according to the present invention, it is possible to program in advance a second imaging plane that is to be imaged next or later with respect to the first imaging plane. Thus, in the conventional technique, a next imaging plane must be determined every time an image is captured and there occurs an interval time between imaging sessions in continuous imaging; however, such an interval time is eliminated according to the present invention and it is possible to sequentially image a plurality of desired phase distributions in the shortest period of time. Such a program can be executed by any clinical MRI apparatus provided with the optical positioning apparatus.

Embodiment 5

A heated point can be more accurately determined by applying a marker 33 beforehand to the heating needle of Embodiment 4, checking the position of the heating needle by the optical positioning apparatus to determine a plane including the region to be heated, and then detecting the marker in an image. For example, by providing a bushing partially covering the heating needle, disposing a plurality of inductor elements (coils) on the bushing, and feeding direct current to the inductor elements or receiving magnetic resonance signals by the inductor elements, it is possible to generate a region in the vicinity of the inductor elements with magnetic field inhomogeneity or with high signal intensity. The position of the marker can be detected as a low-brightness region in an MR image when direct current is fed to the inductor elements, or as a high-brightness region when magnetic resonance signals are received by the inductor elements. It should be noted that a single inductor element may be disposed at the tip of the heating needle to allow for a check of the position of the heated portion.

Moreover, a contrast agent may be applied to the heating needle as a marker to detect the position of the marker as a low-brightness region in an MR image.

Furthermore, an induction electromotive force induced by a plurality of inductor elements disposed on the heating needle in the gradient magnetic field can be detected to numerically detect the position of the inductor elements in proportion to the induction electromotive force.

When a plurality of markers are disposed, a heated region or the like can be accurately detected even if the heating needle bends inside the organ, and the position of the heated point can be more accurately checked as compared to a case in which a check is made only by the optical positioning apparatus. Moreover, a more accurate check of the position of the heated point allows a complex image to be captured in a more appropriate plane, and more accurate temperature measurement of the heated point can be achieved.

Figure 8A:
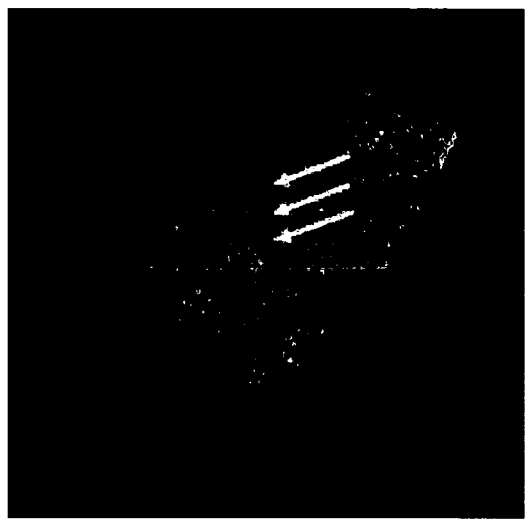
FIG. 8(A) shows an amplitude image with a heating needle provided with a marker.

FIG. 8(A) shows an amplitude image when a microwave heating needle provided with small-diameter coils as inductor elements is inserted into a swine liver and the coils are fed with direct current of 15 mA. In FIG. 8(A), the coils lie at positions indicated by arrows, and their positions are detected as a low-brightness region, i.e., dark points by feeding direct current to them.

Figure 8B:
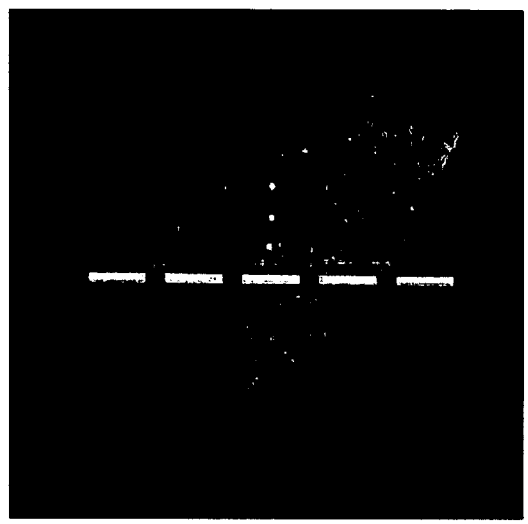
FIG. 8(B) shows determination of an imaging plane from the position of the marker.

Since the heating needle lies on a line connecting these dark points, it is possible to determine a plane perpendicular to the heating needle, as indicted by a dashed line in FIG. 8(B). In this way, the effect of turbulence of the magnetic field generated by the heating needle can be reduced to the least in a complex image captured in a plane perpendicular to the tip of the heating needle, thus allowing for temperature measurement with high accuracy.

Figure 8C:
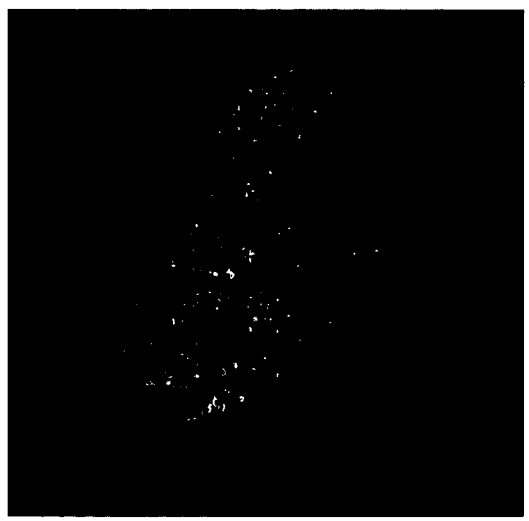
FIG. 8(C) shows display of a temperature distribution in the determined imaging plane superimposed over the amplitude image. More particularly.

A complex image is captured in a plane indicated by a dashed line in FIG. 8(B), a temperature distribution is measured in the vicinity of the heated point according to Embodiment 3 of the present invention, and the result is superimposed over the amplitude image, which is shown in FIG. 8(C).

The present invention will now be described in more detail with reference to examples. However, it should be noted that the present invention is not limited to the examples unless they depart from the scope of the invention.

EXAMPLE 1

In a specific example of Embodiment 1 of the present invention, a living pig (healthy; weight: ca. 20 kg) was put under general anesthesia, then laid in an imaging position in an open MRI gantry, and a microwave heating needle was inserted into its liver to conduct preparatory experimentation on the supposition that microwave thermotherapy was to be applied to a liver cancer. In this example, an MRI apparatus employed was Signa SPi manufactured by GE Medical Systems, and a heating apparatus was Microtase Model AZM-520 manufactured by Azwell, Co., Ltd. (power: 10-110 W).

Figure 9A:
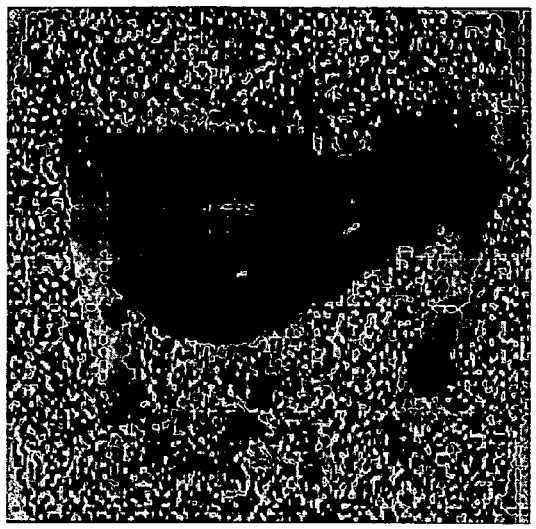
FIG. 9(A) is a phase distribution chart including a heated portion.

First, part of the swine liver was heated like thermotherapy, and a phase distribution of complex signals from water protons after heating was acquired (FIG. 9(A)). In this example, no optical positioning apparatus was employed, and the position of the tip of the heating needle was checked based on a plurality of anatomical images captured by the MRI apparatus.

Figure 9B:
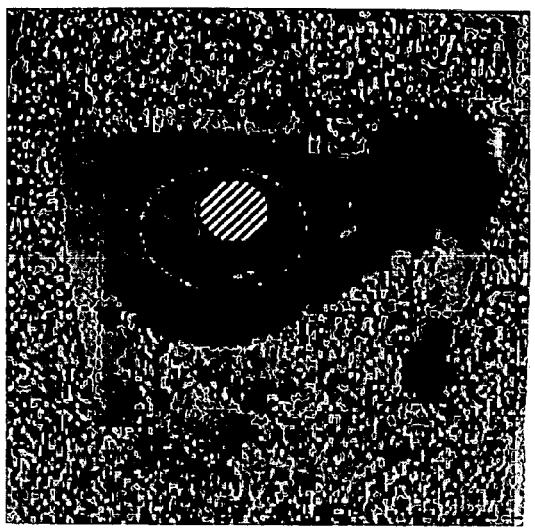
FIG. 9(B) is a phase distribution chart in which a region of interest is defined.
Figure 9C:
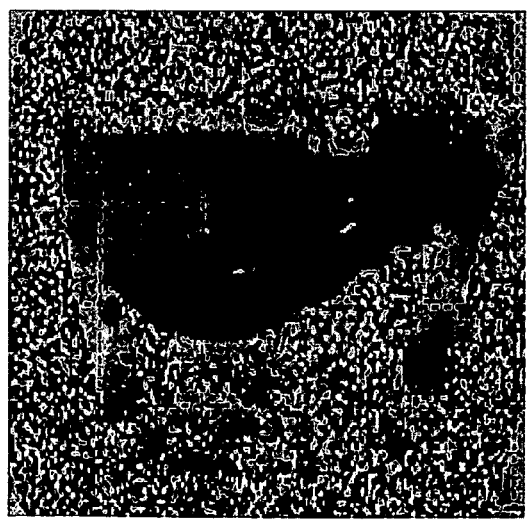
FIG. 9(C) is an estimated phase distribution chart.

A region of interest was defined in each cross-sectional plane of the tip of the heating needle, and a phase distribution before a temperature change was estimated from phase variation in a portion surrounding the region of interest (FIG. 9(B)). In FIG. 9(B), a portion of a hatched circle in the center was defined as a region of interest, and a phase distribution before a temperature change in the region of interest was estimated from a phase distribution in a portion surrounding the region of interest indicated by a white elliptical line. In such an organ as the liver having the inside nearly uniform and the volume larger than that of a portion to be heated, a phase distribution is smooth and a temperature change occurs in a local portion in the organ, and therefore, a phase distribution in the region of interest can be estimated from variation of a phase distribution in the surrounding portion. In this example, a phase distribution was estimated using higher-order rational polynomial fitting by a linear least squares method. An estimated phase distribution including a phase distribution in the region of interest on the assumption that no temperature change takes place is shown in FIG. 9(C). In the drawing, a measured phase in a spatial region that is thought to undergo a temperature rise, i.e., in the region of interest, was temporarily saved in a memory (or an array in a C-language program), a phase distribution in the region of interest before a temperature change was estimated from a phase distribution in the elliptical surrounding portion, and then, the estimated phase distribution was subtracted from the saved original measured phase distribution.

Figure 9D:
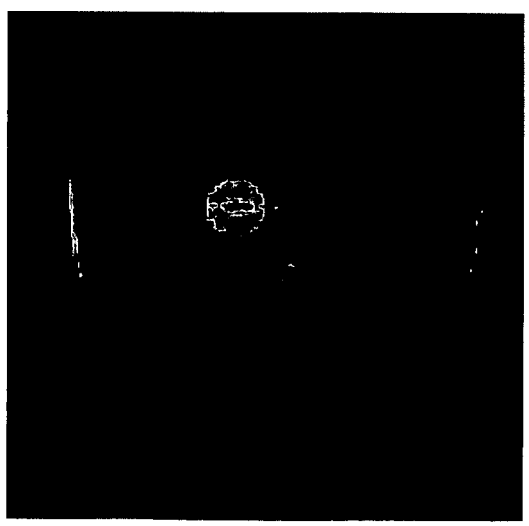
FIG. 9(D) is a temperature change chart superimposed with an anatomical image.
Figure 10A:
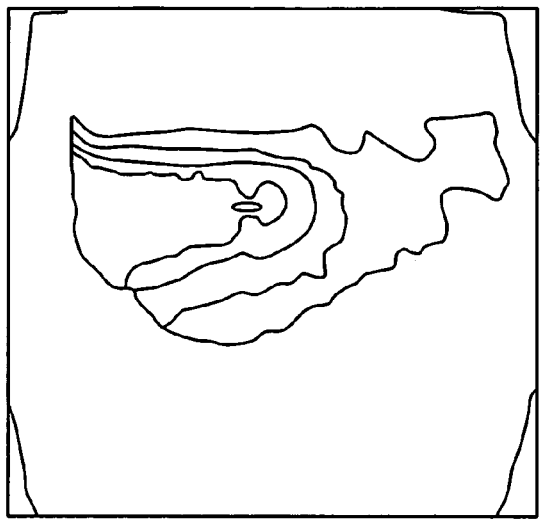
FIG. 10(A) is a schematic chart of FIG. 9(A)
Figure 10B:
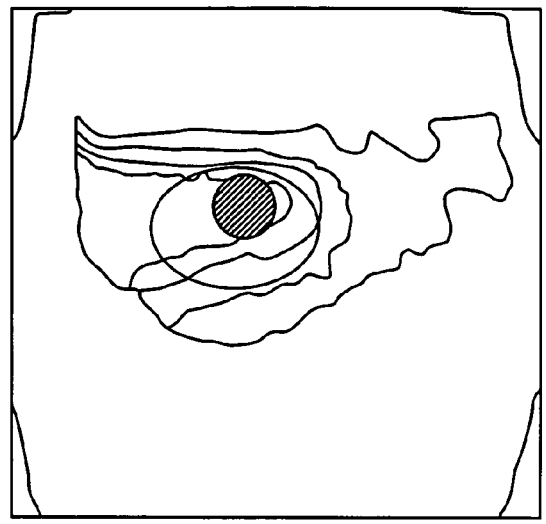
FIG. 10(B) is a schematic chart of FIG. 9(B)
Figure 10C:
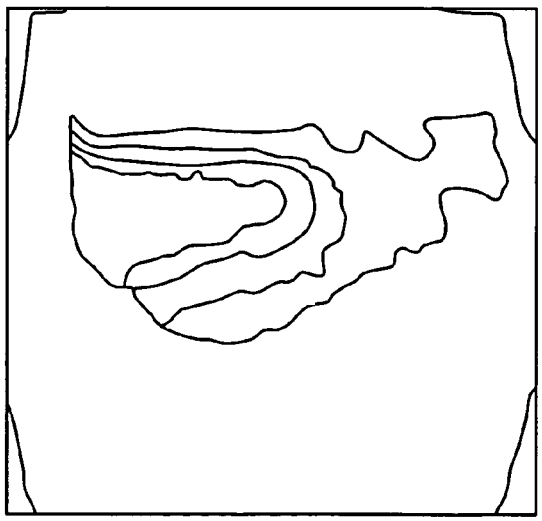
FIG. 10(C) is a schematic chart of FIG. 9(C)
Figure 10D:
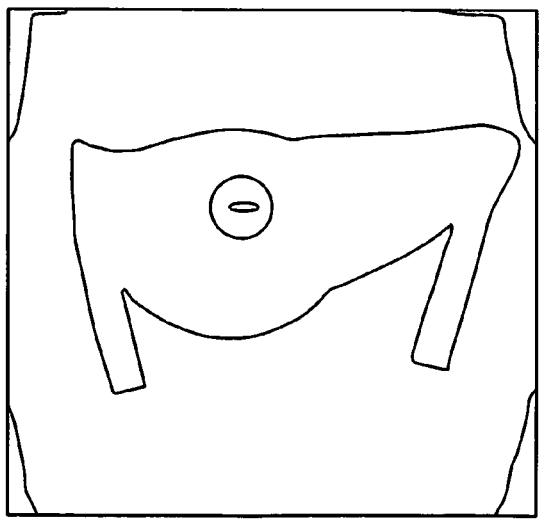
FIG. 10(D) is a schematic chart of FIG. 9(D).

Complex conjugates of the measured phase distribution and estimated phase distribution were multiplied with each other, and an arctangent of the result was calculated for subtraction to measure a temperature change in the vicinity of the tip of the heating needle assumed to be a tumor. A temperature change was determined from the phase variation in the region of interest in this example, and a portion of the temperature change was superimposed over an anatomical image of the swine liver, which is shown in FIG. 9(D). Moreover, FIGS. 10(A)-(D) are schematic charts representing FIGS. 9(A)-(D). FIGS. 10(A)-10(C) schematically show the original phase distribution chart by connecting a border of a portion having the same color with a solid line.

In this example, a phase distribution in the region of interest estimated using higher-order rational polynomial fitting by a linear least squares method closely approximates to a measured phase distribution in the region of interest of the swine liver, in which an error between a measured temperature and an estimated temperature under application of a cubic function was 3.3° C.

COMPARATIVE EXAMPLE 1

A temperature measurement obtained by subtraction of phase distributions before and after heating based on the conventional method and using the same apparatus and the like as that in the present invention resulted in an error between a measured temperature and a calculated temperature of 34.0° C.

EXAMPLE 2

A healthy adult male human subject was laid in an imaging position in the same MRI gantry as that in Example 1, and a phase image and a complex magnetic signal image of a region including the liver were captured to calculate a temperature error in Embodiments 1 and 3 of the present invention. Since no heating was applied, a theoretical temperature change should be 0° C. The measurement was made in a similar manner to that in Example 1, except that the liver of a healthy male human subject was imaged and no heating was applied.

COMPARATIVE EXAMPLE 2

Two phase distribution images were captured in the same imaging plane with the body fixed and respiration held, and the images were subjected to subtraction on a pixel-by-pixel basis to calculate a temperature change according to the conventional method.

As for Example 2 and Comparative Example 2, an average error and a standard deviation (SD) in a circular ROI of a radius of 18 pixels, i.e., an ROI of 1,018 pixels, in one imaging session are shown in Table 1.

TABLE 1

| | | Conventional Method | Self-Referencing Phase Fitting | Self-Referencing Complex Fitting (Inventive Method) |
|---|---|---|---|---|
| No phase transition in ROI | Ave. error [° C.] | 5.65 | 5.06 | 5.22 |
| | SD [° C.] | 4.26 | 3.94 | 3.96 |
| Phase transition in ROI | Ave. error [° C.] | 55.86 | 31.51 | 8.61 |
| | SD [° C.] | 58.12 | 33.14 | 8.23 |

When imaging was conducted in a plane having no phase transition in the region of interest, there was no recognizable difference in an average error between the conventional method in which a temperature change is calculated from a phase difference between two phase distribution images, and two techniques according to the embodiments of the present invention because the position of the liver did not move.

However, when imaging was conducted in a plane having phase transition in the region of interest, the conventional method had an average error greater than 55° C., and Embodiment 1 of the present invention 1 also had an average error greater than 30° C. On the other hand, an average error in Embodiment 3 of the present invention was 8.6° C., which was about ⅐ of that in the conventional method, and about ¼ of that in Embodiment 1.

Thus, even if imaging was conducted in a plane having phase transition in a region of interest, the temperature measurement method according to Embodiment 3 of the present invention was capable of reducing an effect of the phase transition, and achieved temperature measurement of the inside of the liver with a significantly smaller error than that in the conventional method.

As demonstrated by Examples 1 and 2, the method of the present invention has a smaller error between a measured temperature and an estimated temperature than that in the conventional method. In the conventional method, body motion may cause an error between a measured temperature and an estimated temperature as much as several tens of degrees Celsius; on the other hand, the method of the present invention can be regarded as a temperature measurement method fully practical in treatment requiring heating or cooling control in a wide range of temperature.

Thus, according to the method of the present invention, a phase distribution chart can be obtained in an optimal cross-sectional plane by using an optical positioning apparatus even if a region to be measured moves with body motion, and non-invasive temperature measurement on the inside of internal organ or tissue is accurately achieved with an effect of body motion and magnetic field variation completely eliminated by estimating a distribution of phase variation in a region of interest by self referencing to eliminate a process of subtraction between phase distributions before and after a temperature rise.

INDUSTRIAL APPLICABILITY

The present invention overcomes drawbacks in conventional temperature measurement by a phase imaging technique using MRI, whereby accurate temperature measurement of the inside of internal organ or tissue is achieved without being affected by body motion and variation in tissue magnetic susceptibility, and not to mention direct contribution to tumor treatment of animals including human patients by optimal heating control, the present invention may be used as auxiliary means for training of temperature control in thermotherapy or cryotherapy using an experimental animal or an extracted animal organ for a clinician or veterinarian conducting thermotherapy or cryotherapy. Furthermore, the method and apparatus of the present invention also tend to development of medical instruments including a new MRI apparatus, heating apparatus or the like that uses the inventive method and apparatus.

The invention claimed is:

1. A method for measuring a temperature change during a heating or cooling therapeutic procedure in a region of interest inside an object comprising the steps of:

when a local temperature change takes place in a certain position inside an object, acquiring a measured phase distribution image representing a temperature distribution inside said object using, as a temperature indicator, a phase of complex magnetic resonance signals from water protons inside said object observed by a magnetic resonance tomographic imaging technique;

defining a certain position in said acquired measured phase distribution image as a region of interest;

estimating a phase distribution of complex magnetic resonance signals before a temperature change in said region of interest based on a phase distribution of complex magnetic resonance signals in a portion surrounding said region of interest wherein the surrounding portion is subjected to substantially no temperature change;

acquiring an estimated phase distribution image based on said estimated phase distribution;

calculating an amount of phase variation of complex magnetic resonance signals caused by a temperature change in said region of interest by conducting subtraction between said acquired measured phase distribution image and said estimated phase distribution image on a pixel-by-pixel basis; and measuring an amount of a temperature change in said region of interest based on said amount of variation.

2. The method as defined by claim 1, characterized in comprising: estimating a phase distribution of complex magnetic resonance signals in a region of interest by applying higher-order rational polynomial fitting by a linear least squares method, functional fitting by a non-linear least squares method, or a finite element method to a phase distribution of complex magnetic resonance signals in a portion surrounding said region of interest.

3. The method as defined by claim 1, characterized in comprising: conducting subtraction between a measured phase distribution image and an estimated phase distribution image on a pixel-by-pixel basis by multiplying complex conjugates of complex numbers of complex magnetic resonance signals with each other and calculating an arctangent of the product.

4. The method as defined by claim 1, characterized in comprising: outputting a distribution image of the amount of a temperature change based on the amount of phase variation of complex magnetic resonance signals superimposed over an anatomical image of organ or tissue acquired by a magnetic resonance tomographic imaging technique.

5. The method as defined by claim 1, characterized in comprising: capturing a phase distribution image of complex magnetic resonance signals in one, two or three orthogonal planes intersecting an extension of an in-body penetrating portion of a heating or cooling apparatus during thermotreatment or cryo-treatment so as to include a tip of said in-body penetrating portion, or in two or more parallel planes.

6. The method as defined by claim 5, characterized in comprising: checking the position of the tip of the in-body penetrating portion of the heating or cooling apparatus using an optical positioning apparatus, and capturing a phase distribution image of complex magnetic resonance signals so as to include said tip.

7. The method as defined by claim 6, characterized in comprising: providing a marker at the tip of said in-body penetrating portion, and checking a position of the tip of said in-body penetrating portion by detecting said marker in an MRI image or numerically detecting it.

8. The method as defined by claim 7, wherein: the method of providing the marker comprises providing the tip of said in-body penetrating portion with inductor elements or applying a contrast agent to the tip of said in-body penetrating portion.

9. The method as defined by claim 5, characterized in comprising: when target organ or tissue moves with body motion, capturing a phase image of complex magnetic resonance signals following the movement or covering a range of the movement.

10. A method for measuring a temperature change during a heating or cooling therapeutic procedure in a region of interest inside an object comprising the steps of:

when a local temperature change takes place in a certain position inside an object, acquiring a real-part image and an imaginary-part image as measured complex images incorporating a temperature distribution inside said object using, as a temperature indicator, a phase of complex magnetic resonance signals from water protons inside said object observed by a magnetic resonance tomographic imaging technique;

defining the same position in said acquired real-part and imaginary-part images as a region of interest;

estimating a distribution of a real part and an imaginary part of complex magnetic resonance signals before a temperature change in said region of interest based on a distribution of a real part and an imaginary part of complex magnetic resonance signals in a portion surrounding said region of interest wherein the surrounding portion is subjected to substantially no temperature change;

acquiring an estimated complex image based on said estimated real-part and imaginary-part distribution;

calculating an amount of phase variation of complex magnetic resonance signals caused by a temperature change in said region of interest by calculating a phase difference between said measured complex image and said estimated complex image on a pixel-by-pixel basis; and measuring an amount of a temperature change in said region of interest based on said amount of variation.

11. The method as defined by claim 10, characterized in comprising: estimating a distribution of a real part and an imaginary part of complex magnetic resonance signals in a region of interest by applying higher-order rational polynomial fitting by a linear least squares method, functional fitting by a non-linear least squares method, or a finite element method to a distribution of a real part and an imaginary part of complex magnetic resonance signals in a portion surrounding said region of interest.

12. The method as defined by claim 10, characterized in comprising: calculating a phase difference between a measured complex image and an estimated complex image on a pixel-by-pixel basis by multiplying complex conjugates of complex numbers of complex magnetic resonance signals with each other and calculating an arctangent of a ratio between a real part and an imaginary part of the product.

13. The method as defined by claim 10, characterized in comprising: outputting a distribution image of the amount of a temperature change based on the amount of phase variation of complex magnetic resonance signals superimposed over an anatomical image of organ or tissue acquired by a magnetic resonance tomographic imaging technique.

14. The method as defined by claim 10, characterized in comprising: capturing a phase distribution image of complex magnetic resonance signals in one, two or three orthogonal planes intersecting an extension of an in-body penetrating portion of a heating or cooling apparatus during thermo-treatment or cryo-treatment so as to include a tip of said in-body penetrating portion, or in two or more parallel planes.

15. The method as defined by claim 14, characterized in comprising: checking the position of the tip of the in-body penetrating portion of the heating or cooling apparatus using an optical positioning apparatus, and capturing a phase distribution image of complex magnetic resonance signals so as to include said tip.

16. The method as defined by claim 15, characterized in comprising: providing a marker at the tip of said in-body penetrating portion, and checking a position of the tip of said in-body penetrating portion by detecting said marker in an MRI image or numerically detecting it.

17. The method as defined by claim 16, wherein: the method of providing the marker comprises providing the tip of said in-body penetrating portion with inductor elements or applying a contrast agent to the tip of said in-body penetrating portion.

18. The method as defined by any one of claim 14, characterized in comprising: when target organ or tissue moves with body motion, capturing a phase image of complex magnetic resonance signals following the movement or covering a range of the movement.

19. A temperature change measurement apparatus for measuring a temperature change during a heating or cooling therapeutic procedure in a region of interest inside an object comprising:
means for, when a local temperature change takes place in a certain position inside an object, producing a measured phase distribution image representing a temperature distribution of said object using, as a temperature indicator, a phase of complex magnetic resonance signals from water protons inside said object observed by a magnetic resonance tomographic imaging technique;
means for defining a region of interest in said acquired measured phase distribution image;
means for estimating a phase distribution of complex magnetic resonance signals before a temperature change in said region of interest based on a phase distribution of complex magnetic resonance signals in a portion surrounding said region of interest wherein the surrounding portion is subjected to substantially no temperature change;
means for producing an estimated phase distribution image based on said estimated phase distribution;
means for producing a phase difference distribution image from a phase difference in complex magnetic resonance signals caused by a temperature change in said region of interest by conducting subtraction between said acquired measured phase distribution image and said estimated phase distribution image on a pixel-by-pixel basis; and
means for calculating a temperature change from said phase difference distribution image.

20. The apparatus as defined by claim 19, characterized in that: said means for estimating a phase distribution applies higher-order rational polynomial fitting by a linear least squares method, functional fitting by a non-linear least squares method, or a finite element method to a phase distribution of complex magnetic resonance signals in a portion surrounding said region of interest.

21. The apparatus as defined by claim 19, characterized in that: said means for producing a phase difference distribution image conducts subtraction between a measured phase distribution image and an estimated phase distribution image on a pixel-by-pixel basis by multiplying complex conjugates of complex numbers of complex magnetic resonance signals with each other and calculating an arctangent of the product.

22. The apparatus as defined by claim 19, comprising: in addition to said means for producing a phase difference distribution image representing the amount of phase variation of complex magnetic resonance signals caused by a temperature change in a region for interest, means of outputting a temperature image calculated from said phase difference distribution image superimposed over an anatomical image of organ or tissue.

23. The apparatus as defined by claim 19, characterized in comprising: to capture a measured phase distribution image or measured complex image, means for checking a tip of an in-body penetrating portion of a heating or cooling apparatus, and capturing a phase distribution image or a complex image of complex magnetic resonance signals in one, two or three orthogonal planes intersecting an extension of the in-body penetrating portion of the heating or cooling apparatus, or in two or more parallel planes.

24. The apparatus as defined by claim 23, characterized in that: a position of the tip of the in-body penetrating portion of the heating or cooling apparatus is checked using an optical positioning apparatus.

25. The apparatus as defined by claim 24, characterized in that: a marker is provided at the tip of said in-body penetrating portion, and the position of the tip of said in-body penetrating portion is further checked by detecting said marker by an MRI apparatus.

26. The apparatus as defined by claim 25, characterized in that: said means for providing a marker provides the tip for said in-body penetrating portion with inductor elements or applies a contrast agent to the tip of said in-body penetrating portion.

27. The apparatus as defined by claim 24, characterized in that: when target organ or tissue moves with body motion, the position of the tip of the in-body penetrating portion of the heating or cooling apparatus is checked following the movement or covering a range of the movement.

28. A temperature change measurement apparatus for measuring a temperature change during a heating or cooling therapeutic procedure in a region of interest inside an object comprising:

means for, when a local temperature change takes place in a certain position inside an object, producing a real-part image and an imaginary-part image as measured complex images incorporating a temperature distribution of said object using, as a temperature indicator, a phase of complex magnetic resonance signals from water protons inside said object observed by a magnetic resonance tomographic imaging technique;

means for defining a region of interest in said acquired measured complex image;

means for estimating a complex image before a temperature change in said region of interest based on a distribution of a real part and an imaginary part of complex magnetic resonance signals in a portion surrounding said region of interest wherein the surrounding portion is subjected to substantially no temperature change;

means for producing an image representing the amount of phase variation of complex magnetic resonance signals caused by a temperature change in said region of interest by calculating a phase difference between said acquired measured complex image and said estimated complex image on a pixel-by-pixel basis; and means for calculating a temperature change from said phase distribution image.

29. The apparatus as defined by claim 28, characterized in that: said means for estimating a phase distribution applies higher-order rational polynomial fitting by a linear least squares method, functional fitting by a non-linear least squares method, or a finite element method to a distribution of a real part and an imaginary part of complex magnetic resonance signals in a portion surrounding said region of interest.

30. The apparatus as defined by claim 28, characterized in that: said means for producing a phase difference distribution image calculates a phase difference between a measured complex image and an estimated complex image on a pixel-by-pixel basis by multiplying complex conjugates of complex numbers of complex magnetic resonance signals with each other and calculating an arctangent of the ratio between a real part and an imaginary part of the product.

31. The apparatus as defined by claim 28, characterized in comprising: in addition to said means for producing a phase difference distribution image representing the amount of phase variation of complex magnetic resonance signals caused by a temperature change in a region for interest, means of outputting a temperature image calculated from said phase difference distribution image superimposed over an anatomical image of organ or tissue.

32. The apparatus as defined by claim 28, characterized in comprising: to capture a measured phase distribution image or measured complex image, means for checking a tip of an in-body penetrating portion of a heating or cooling apparatus, and capturing a phase distribution image or a complex image of complex magnetic resonance signals in one, two or three orthogonal planes intersecting an extension of the in-body penetrating portion of the heating or cooling apparatus, or in two or more parallel planes.

33. The apparatus as defined by claim 32, characterized in that: a position of the tip of the in-body penetrating portion of the heating or cooling apparatus is checked using an optical positioning apparatus.

34. The apparatus as defined by claim 33, characterized in that: a marker is provided at the tip of said in-body penetrating portion, and the position of the tip of said in-body penetrating portion is further checked by detecting said marker by an MRI apparatus.

35. The apparatus as defined by claim 34, characterized in that: said means of providing a marker provides the tip for said in-body penetrating portion with inductor elements or applies a contrast agent to the tip of said in-body penetrating portion.

36. The apparatus as defined by claim 33, characterized in that: when target organ or tissue moves with body motion, the position of the tip of the in-body penetrating portion of the heating or cooling apparatus is checked following the movement or covering a range of the movement.

* * * * *

UNITED STATES PATENT AND TRADEMARK OFFICE
CERTIFICATE OF CORRECTION

PATENT NO. : 7,505,805 B2 Page 1 of 1
APPLICATION NO. : 10/564169
DATED : March 17, 2009
INVENTOR(S) : Kuroda It is certified that error appears in the above-identified patent and that said Letters Patent is hereby corrected as shown below:

On the Title page Item (73) Assignee, after "Foundation for Biomedical Research and Innovation, Hyogo (JP)" insert --; GE Medical Systems Global Technology Company, LLC, Waukesha, WI (US)--.

Signed and Sealed this

Thirtieth Day of June, 2009

JOHN DOLL
*Acting Director of the United States Patent and Trademark Office*